US012784226B2

(12) United States Patent
Gogna et al.

(10) Patent No.: US 12,784,226 B2
(45) Date of Patent: Nov. 3, 2026

(54) SYSTEMS AND METHODS FOR AUTOMATED VIEW PLANE DETECTION FOR ULTRASOUND EXAMINATION

(71) Applicant: GE Precision Healthcare LLC, Wauwatosa, WI (US)

(72) Inventors: Anuprriya Gogna, Vöcklabruck (AT); Vikram Melapudi, Bengaluru (IN); Rahul Venkataramani, Bengaluru (IN)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 995 days.

(21) Appl. No.: 17/651,770

(22) Filed: Feb. 18, 2022

(65) Prior Publication Data

US 2023/0267618 A1 Aug. 24, 2023

(51) Int. Cl.

| | |
|---|---|
| ***G06T 7/12*** | (2017.01) |
| ***A61B 8/00*** | (2006.01) |
| ***A61B 8/08*** | (2006.01) |
| ***G06T 7/00*** | (2017.01) |
| ***G06T 11/00*** | (2006.01) |
| ***G16H 30/40*** | (2018.01) |

(52) U.S. Cl.

CPC .................. *G06T 7/12* (2017.01); *A61B 8/08* (2013.01); *A61B 8/463* (2013.01); *A61B 8/523* (2013.01); *G06T 7/0012* (2013.01); *G06T 11/00* (2013.01); *G16H 30/40* (2018.01); *G06T 2207/10136* (2013.01); *G06T 2207/20081* (2013.01); *G06T 2207/30004* (2013.01)

(58) Field of Classification Search

CPC ......... G06T 7/12; G06T 7/0012; G06T 11/00; G06T 2207/10136; G06T 2207/20081; G06T 2207/30004; G06T 2207/20084; A61B 8/08; A61B 8/463; A61B 8/523; A61B 8/4427; A61B 8/085; A61B 8/0866; A61B 8/483; A61B 8/5223; A61B 8/469; A61B 8/466; A61B 8/5215; G16H 30/40; G16H 50/70; G16H 50/20

See application file for complete search history.

(56) References Cited

U.S. PATENT DOCUMENTS

| | | | | |
|---|---|---|---|---|
| 12,279,906 B2 * | 4/2025 | Ciofolo-Veit | .......... | A61B 8/523 |
| 2018/0000441 A1 * | 1/2018 | Wang | ........................ | G06T 7/11 |
| 2018/0338745 A1 * | 11/2018 | Takeuchi | ............. | A61B 8/4218 |
| 2020/0085382 A1 * | 3/2020 | Taerum | .................. | A61B 5/055 |

(Continued)

OTHER PUBLICATIONS

English Machine Translation of CN 108062749 A (Ni et al., Published Apr. 21, 2020) (Year: 2020).*

(Continued)

*Primary Examiner* — Juan M Guillermety

(74) *Attorney, Agent, or Firm* — McCoy Russell LLP

(57) ABSTRACT

Methods and systems are provided for an automated ultrasound exam. In one example, a method includes identifying a view plane of interest based on one or more 3D ultrasound images, obtaining a view plane image including the view plane of interest from a 3D volume of ultrasound data of a patient, where the one or more 3D ultrasound images are generated from the 3D volume of ultrasound data, segmenting an anatomical region of interest (ROI) within the view plane image to generate a contour of the anatomical ROI, and displaying the contour on the view plane image.

11 Claims, 9 Drawing Sheets

(56) References Cited

U.S. PATENT DOCUMENTS

| | | | | |
|---|---|---|---|---|
| 2020/0383658 | A1* | 12/2020 | Wang | A61B 8/467 |
| 2021/0201066 | A1* | 7/2021 | Cui | G06T 7/11 |
| 2021/0251601 | A1* | 8/2021 | Han | A61B 8/466 |
| 2024/0050024 | A1* | 2/2024 | Sham | A61B 8/4416 |

OTHER PUBLICATIONS

Provisional Application of U.S PreGrant 2024/0050024 (Year: 2021).*

Sindhwani, N. et al., "Semi-automatic outlining of levator hiatus," Ultrasound in Obstetrics & Gynecology, vol. 48, No. 1, Jul. 2016, Available Online Oct. 5, 2015, 19 pages.

Williams, H. et al., "Automatic C-Plane Detection in Pelvic Floor Transperineal Volumetric Ultrasound," Proceedings of the First International Workshop, ASMUS 2020, and 5th International Workshop, PIPPI 2020, Held in Conjunction with MICCAI 2020, Oct. 4, 2020, Lima, Peru, 11 pages.

* cited by examiner

SYSTEMS AND METHODS FOR AUTOMATED VIEW PLANE DETECTION FOR ULTRASOUND EXAMINATION

TECHNICAL FIELD

Embodiments of the subject matter disclosed herein relate to ultrasound imaging, and more particularly, to an automated, ultrasound-based pelvic floor examination.

BACKGROUND

Medical ultrasound is an imaging modality that employs ultrasound waves to probe the internal structures of a body of a patient and produce a corresponding image. For example, an ultrasound probe comprising a plurality of transducer elements emits ultrasonic pulses which reflect or echo, refract, or are absorbed by structures in the body. The ultrasound probe then receives reflected echoes, which are processed into an image. Ultrasound images of the internal structures may be saved for later analysis by a clinician to aid in diagnosis and/or displayed on a display device in real time or near real time.

SUMMARY

In an embodiment, a method includes identifying a view plane of interest based on one or more 3D ultrasound images, obtaining a view plane image including the view plane of interest from a 3D volume of ultrasound data of a patient, where the one or more 3D ultrasound images are generated from the 3D volume of ultrasound data, segmenting an anatomical region of interest (ROI) within the view plane image to generate a contour of the anatomical ROI, and displaying the contour on the view plane image.

The above advantages and other advantages, and features of the present description will be readily apparent from the following Detailed Description when taken alone or in connection with the accompanying drawings. It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

Various aspects of this disclosure may be better understood upon reading the following detailed description and upon reference to the drawings in which.

DETAILED DESCRIPTION

Figure 1:
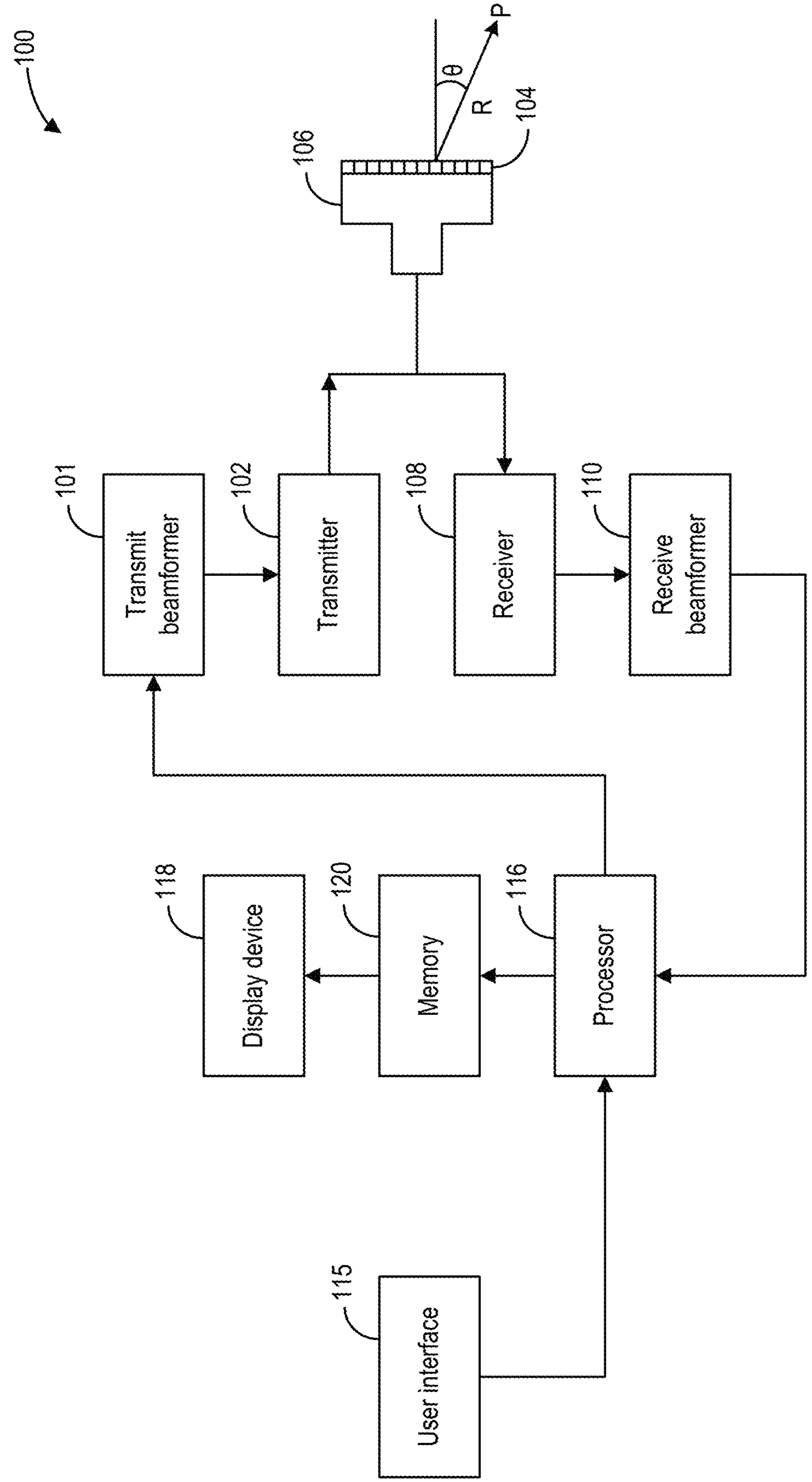
FIG. 1 shows a block diagram of an embodiment of an ultrasound system.

Pelvic floor examinations using ultrasound may be useful to evaluate the health of the pelvic floor, including but not limited to the bladder, levator ani muscle, urethra, and vagina. Ultrasound-based pelvic floor examinations may help determine the integrity of pelvic muscles and ascertain the necessity of corrective actions including surgical interventions. A complete pelvic floor examination of a patient may include a series of dynamic exams with both 2D and 3D acquisitions, which are highly dependent on the patient's involvement (e.g., commanded muscle maneuvers by the patient) and operator expertise. For example, one or more 3D renderings may be acquired to view the anatomical region of interest, and then a series of 3D renderings may be acquired while the patient is asked to push down and/or contract the pelvic floor muscles. Further, the examination includes several measurements on the acquired images. Accordingly, standard pelvic floor examinations require highly trained operators and may be time-consuming and mentally burdensome for both the patients and the operators.

For example, the measurements may include dimensions of the levator hiatus (e.g., area, and lateral as well as anterior-posterior diameters), which is an opening in the pelvic floor defined by the levator ani muscle and the inferior pubic rami. The dimensions of the levator hiatus may be measured during muscle contraction and expansion (e.g., during Valsalva) in order to assess the structural integrity of the levator ani muscle, possible pelvic organ prolapse, and proper functioning and strength of the pelvic floor muscles.

During a standard pelvic floor examination, an ultrasound operator may hold an ultrasound probe on a patient in a given position while the patient performs breath holds, contracts and/or pushes down the pelvic floor muscles, or performs other activities. As such, image quality may vary from exam to exam. Further, the presentation of the imaged pelvic floor muscles can vary from patient to patient, and thus highly trained operators may be necessary to ensure the correct image slice (e.g., showing the plane of minimal hiatal dimension) is selected for analysis (from among a plurality of image slices acquired as part of a 3D volume of ultrasound data). The operator may identify the appropriate initial volume image (e.g., an image frame from the 3D volume), identify the view plane of interest (e.g., the plane of minimal hiatal dimension) in the selected volume image, annotate the view plane of interest with the levator hiatus contour, and perform various measurements on the levator hiatus, such as area, circumference, lateral diameter, and anterior-posterior diameter. Each step may be time-consuming, which may be further exacerbated if low image quality results in the operator having to reacquire certain images or volumes of data.

Thus, according to embodiments disclosed herein, artificial-intelligence based methods may be applied to automate aspects of the pelvic floor examination. As explained in more detail below, a view plane of interest (e.g., the plane including the minimal hiatal dimension) may be automatically identified in a 3D ultrasound image. Once the view plane of interest is identified, a set of deep learning models may be deployed to automatically segment the levator hiatus boundary, as well as mark the two diameters (e.g., the lateral and anterior-posterior diameters) on the plane of the minimal hiatal dimension for the ascertainment of the various measurements and subsequently health/integrity of the levator muscles. This process may be repeated as the patient performs breath holds, contracts the pelvic floor muscles, etc. In doing so, clinical outcomes may be improved by increased accuracy and robustness of the pelvic exams, operator and patient experience may be improved due to reduced examination and analysis time, and reliance on highly trained operators may be reduced.

While the disclosure presented herein is directed to a pelvic floor examination where the plane of minimal hiatal dimension is identified within a volume of ultrasound data and the levator hiatus is segmented using a set of deep learning models to initially identify and then measure aspects of the levator hiatus, the framework provided herein may be applied to automate other medical imaging exams that rely on identification of a slice from a volume of data and/or segmentation of an anatomical region of interest.

Figure 3:
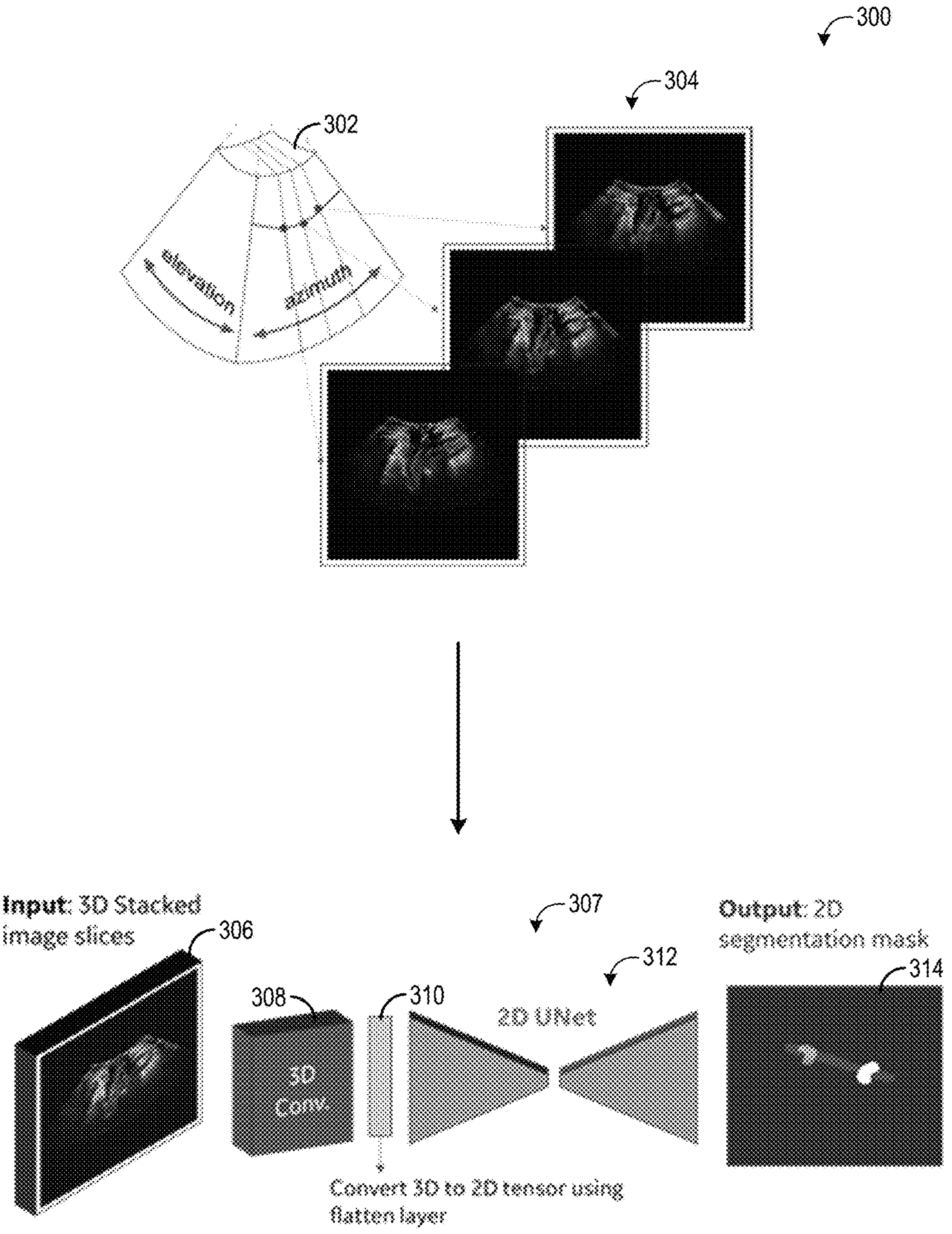
FIG. 3 schematically shows an example process for generating a 2D segmentation mask identifying a view plane of interest using 3D stacked image slices as input.
Figure 4:
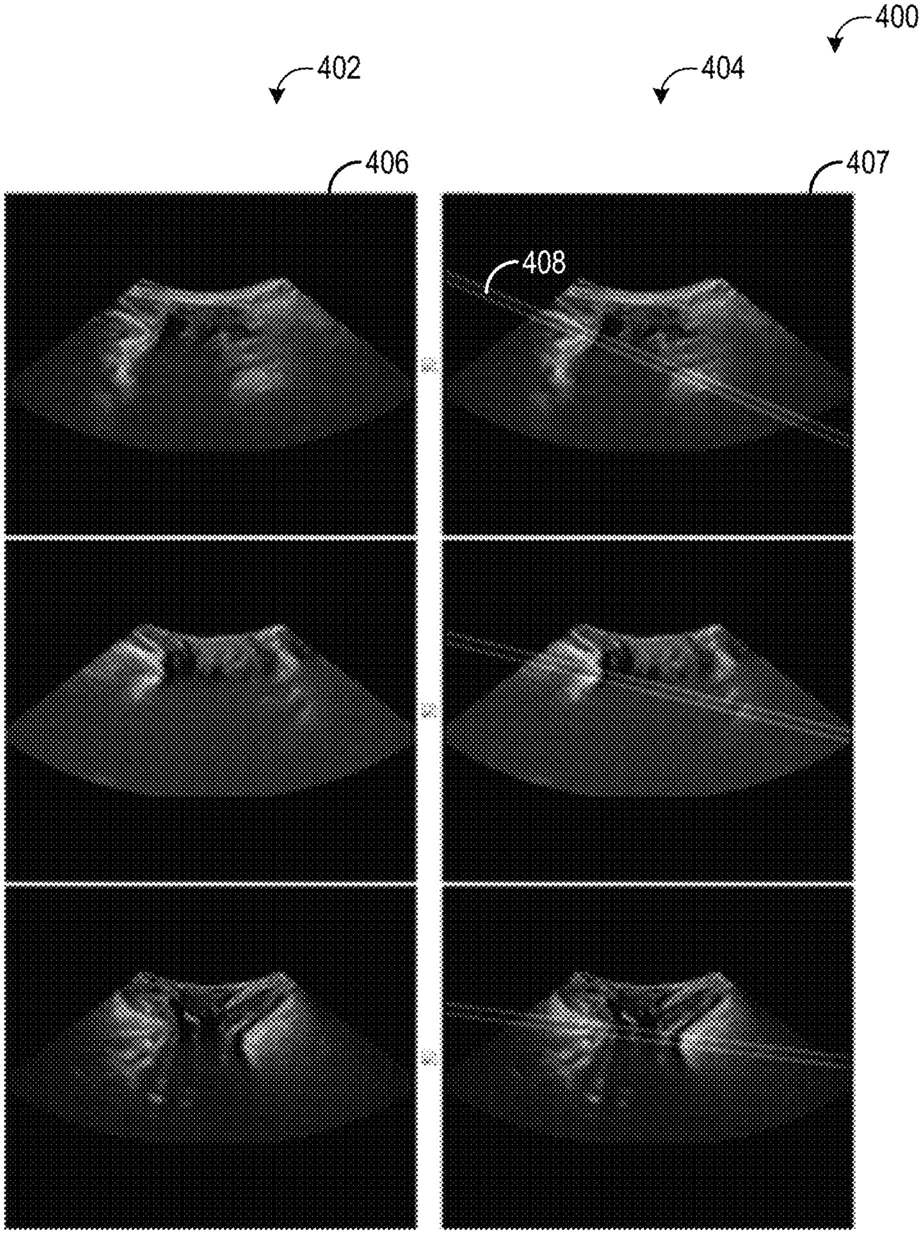
FIG. 4 shows example input images and output identifications of corresponding view planes of interest.
Figure 5:
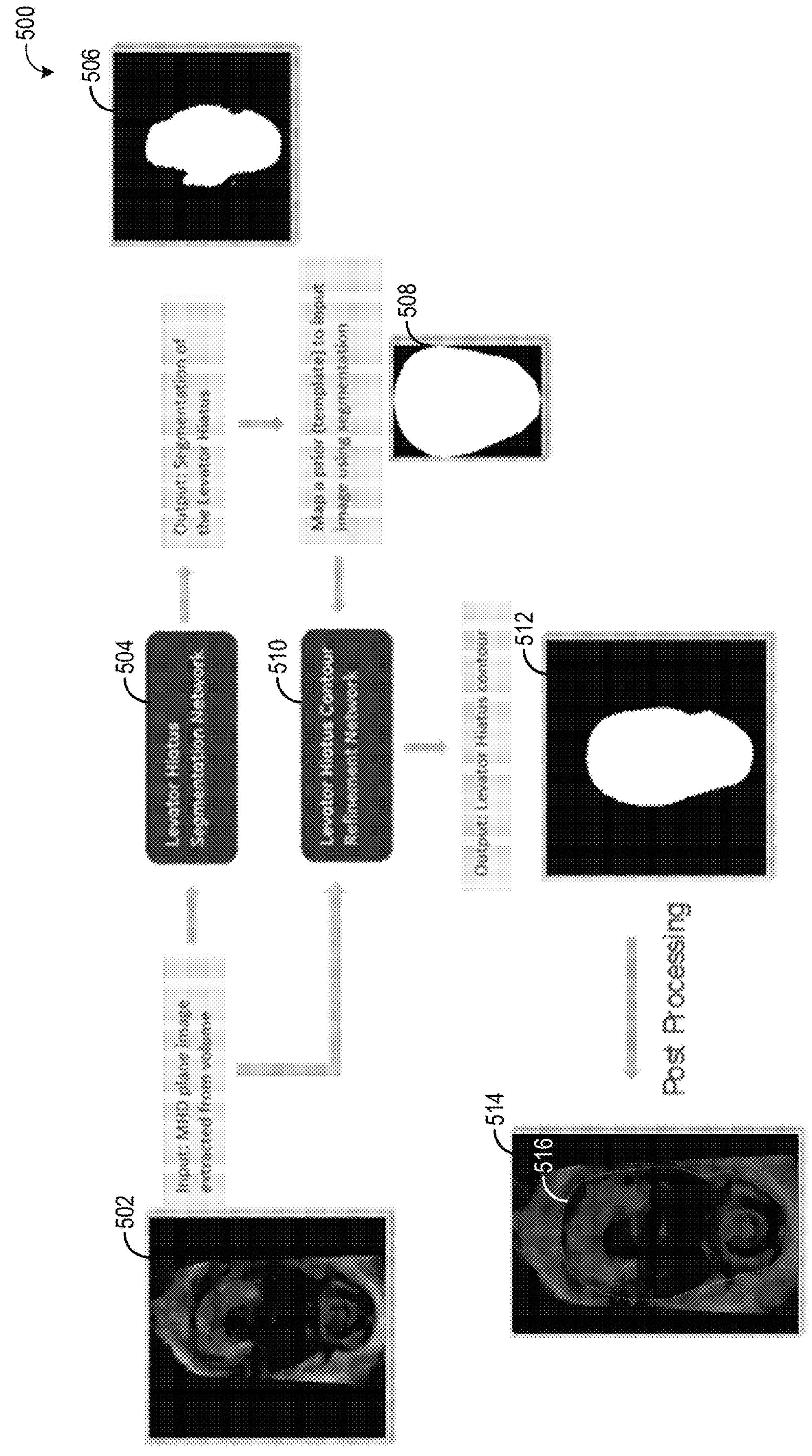
FIG. 5 schematically shows an example process for generating and refining a segmentation contour of an anatomical region of interest.
Figure 6:
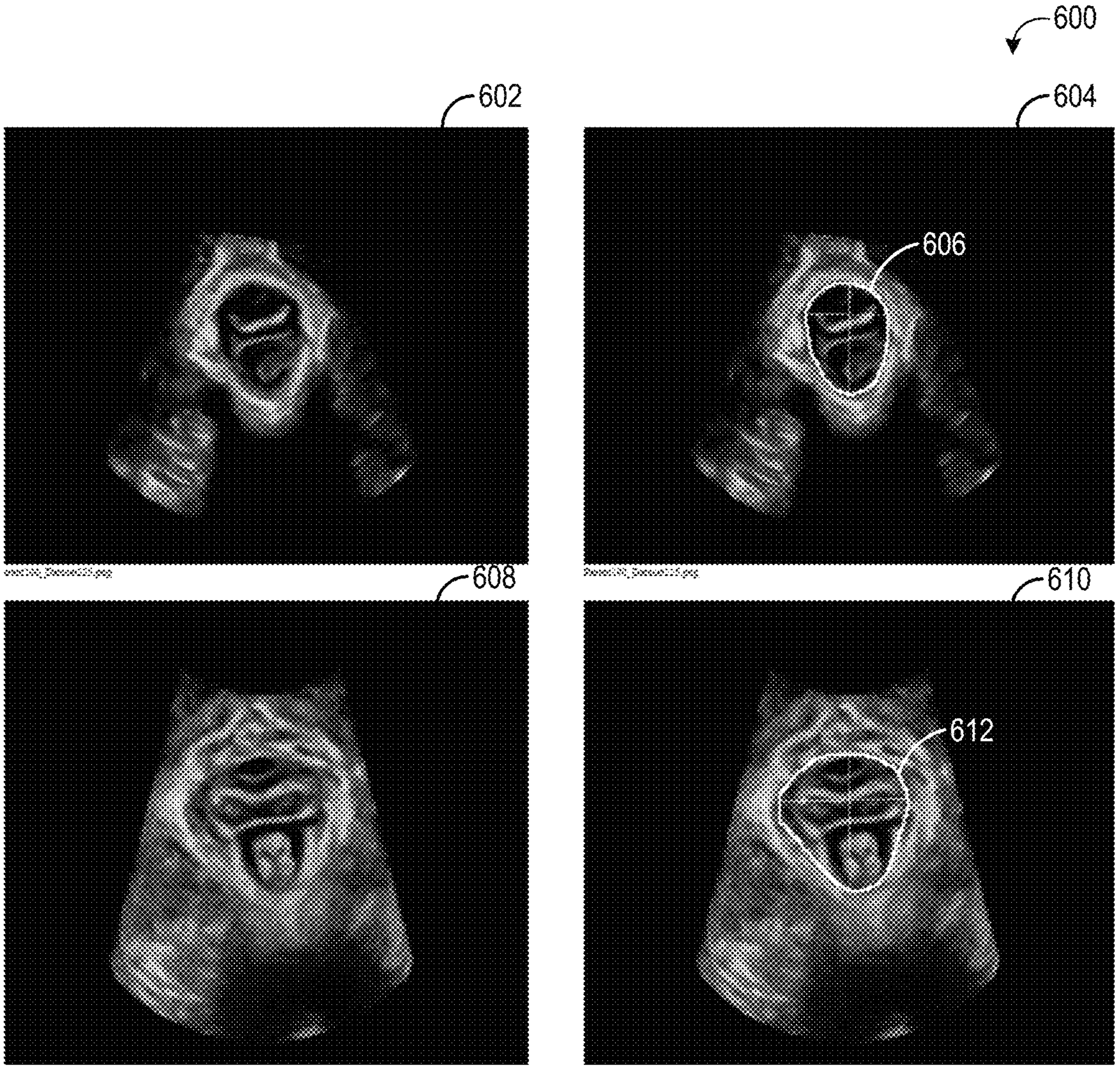
FIG. 6 shows examples of contours of an anatomical region of interest generated according to the process of FIG. 5.
Figure 7:
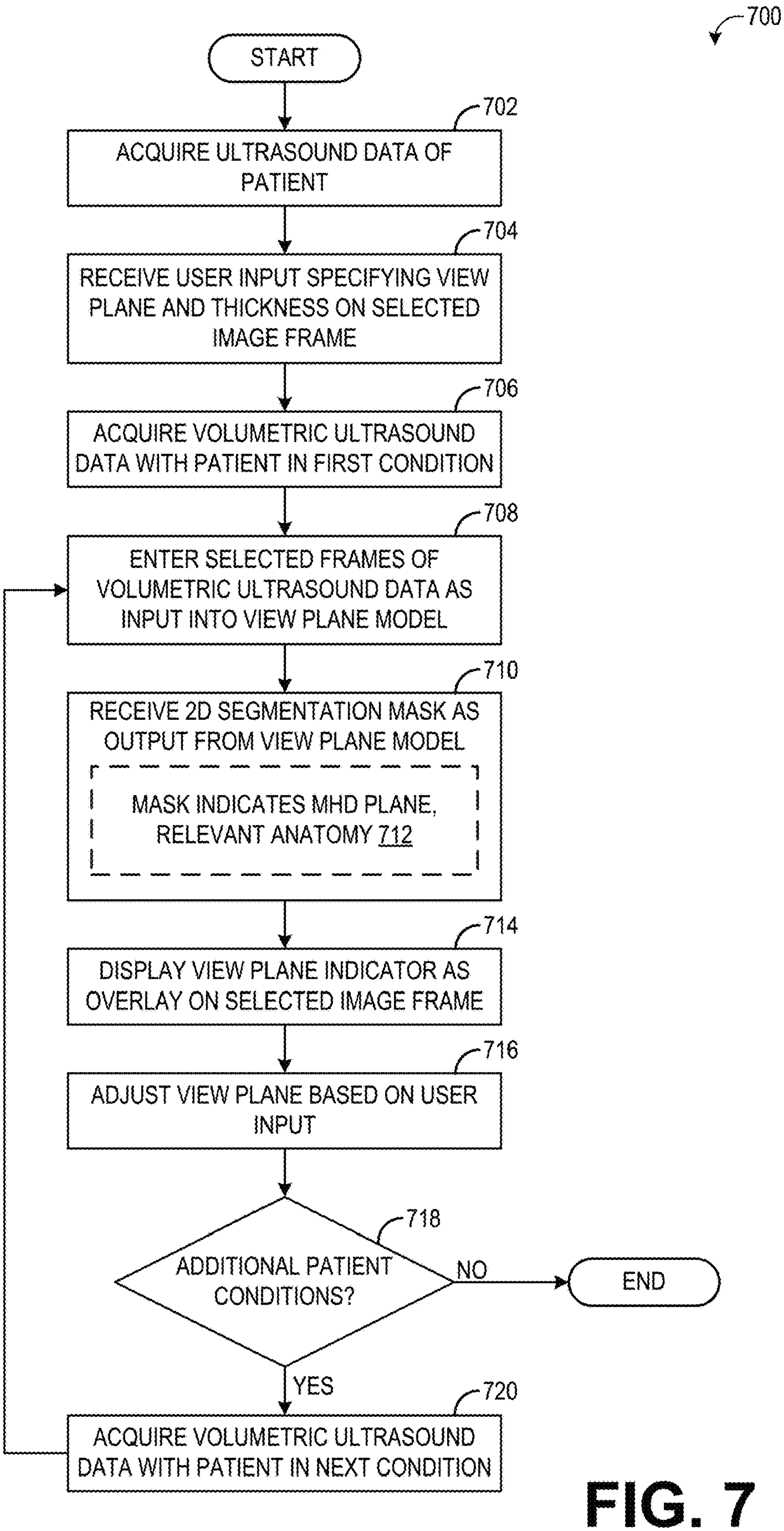
FIG. 7 is a flow chart illustrating a method for identifying a view plane of interest.
Figure 8:
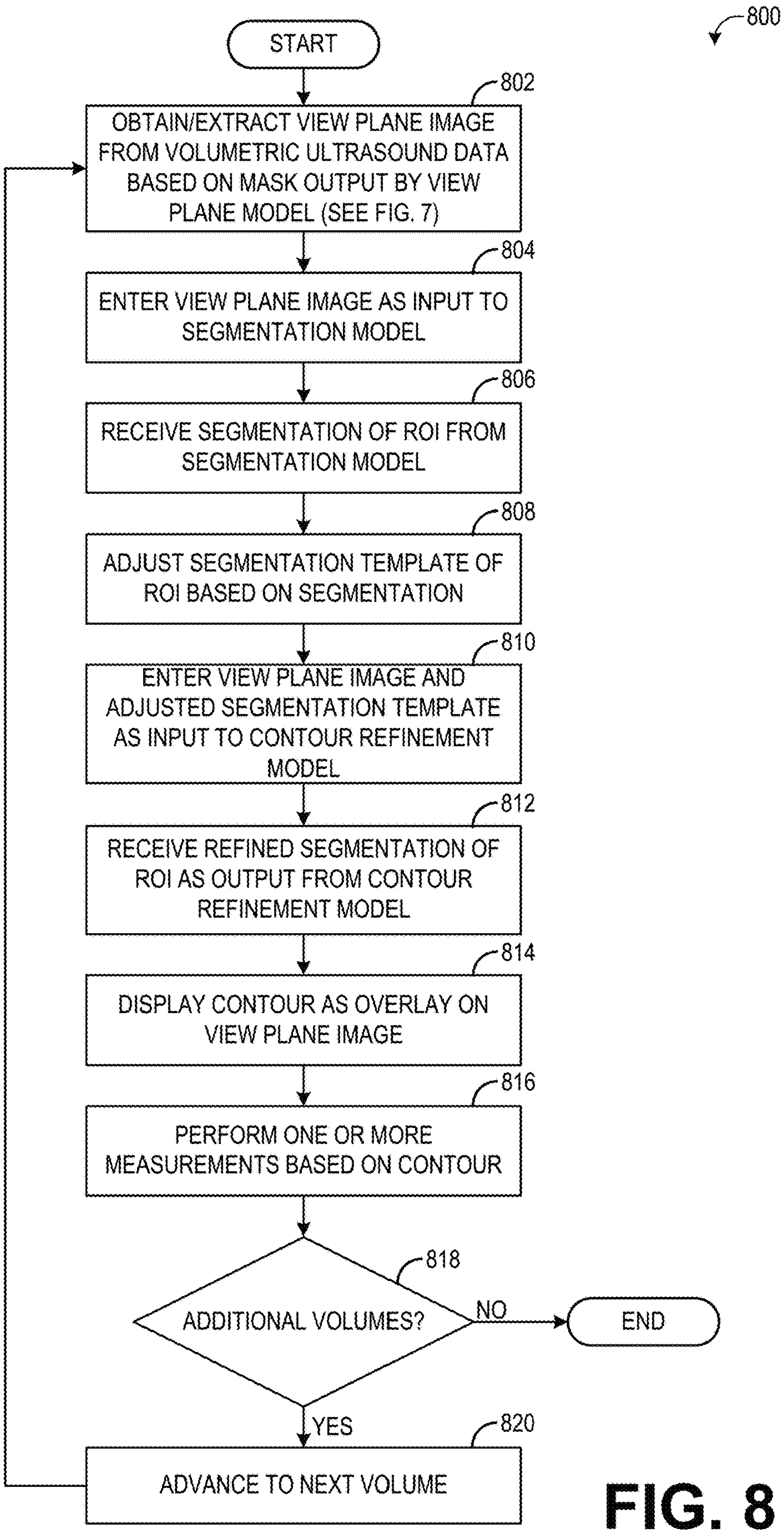
FIG. 8 is a flow chart illustrating a method for generating a contour of an anatomical region of interest.
Figure 9:
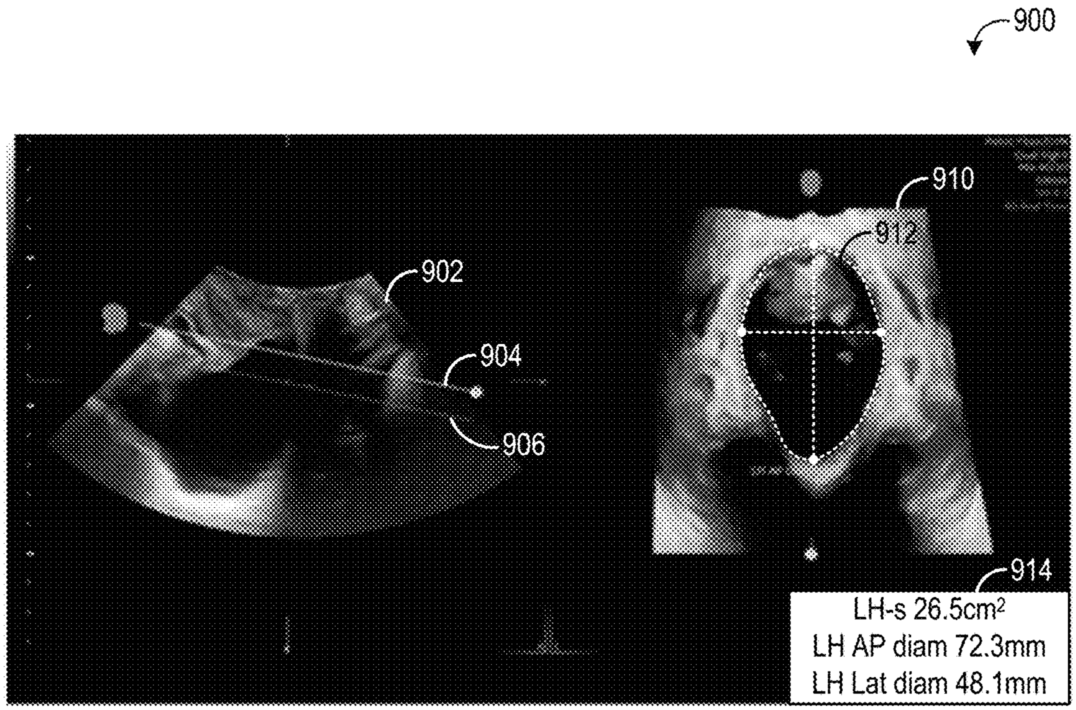
FIGS. 9 and 10 show example user interfaces displaying view planes of interest and overlying contours of an anatomical region of interest.
Figure 10:
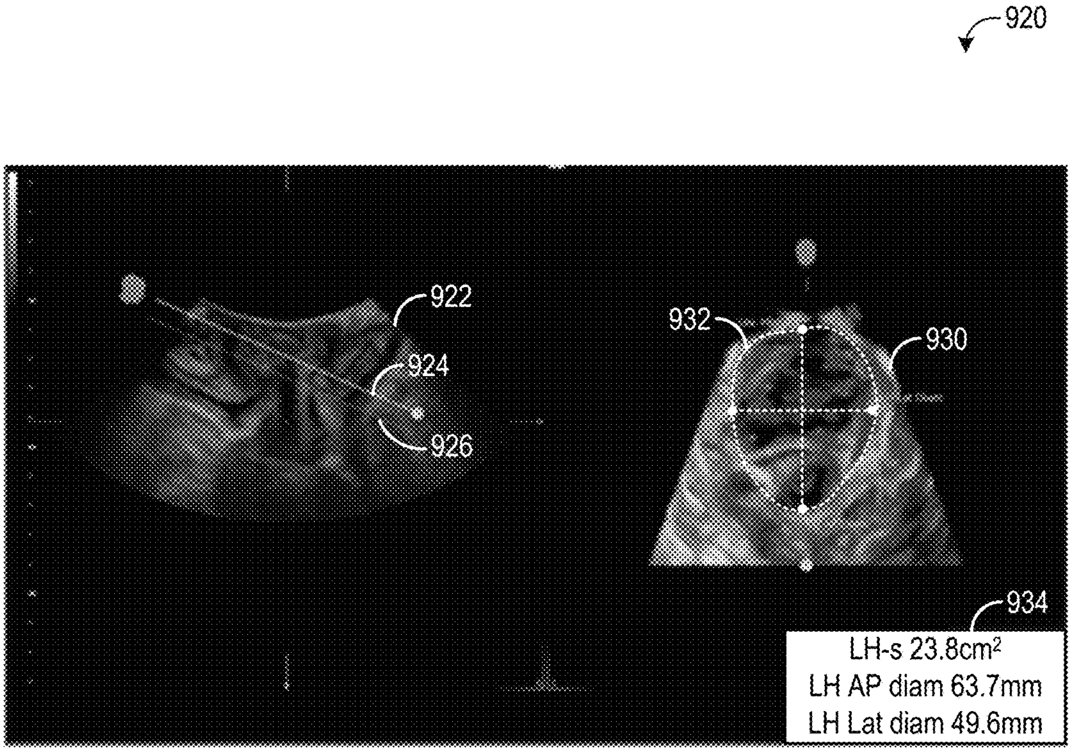

An example ultrasound system including an ultrasound probe, a display device, and an imaging processing system are shown in FIG. 1. Via the ultrasound probe, ultrasound data may be acquired, and ultrasound images generated from the ultrasound data (which may include 2D images, 3D renderings, and/or slices of a 3D volume) may be displayed on the display device. The ultrasound images/volume may be processed by an image processing system, such as the image processing system of FIG. 2, to identify a view plane of interest, segment an anatomical region of interest (ROI), and perform measurements based on a contour of the anatomical ROI. FIG. 3 shows a process for identifying a view plane of interest from selected 3D images of a volumetric ultrasound dataset, examples of which are shown in FIG. 4. FIG. 5 shows a process for segmenting an anatomical ROI (e.g., levator hiatus) and generating a contour of the anatomical ROI, examples of which are shown in FIG. 6. A method for identifying a view plane of interest is illustrated in FIG. 7 and a method for generating a contour of an anatomical ROI is shown in FIG. 8. FIGS. 9 and 10 show example graphical user interfaces via which view plane identifications and corresponding anatomical ROI contour identifications may be displayed.

Referring to FIG. 1, a schematic diagram of an ultrasound imaging system 100 in accordance with an embodiment of the disclosure is shown. The ultrasound imaging system 100 includes a transmit beamformer 101 and a transmitter 102 that drives elements (e.g., transducer elements) 104 within a transducer array, herein referred to as probe 106, to emit pulsed ultrasonic signals (referred to herein as transmit pulses) into a body (not shown). According to an embodiment, the probe 106 may be a one-dimensional transducer array probe. However, in some embodiments, the probe 106 may be a two-dimensional matrix transducer array probe. As explained further below, the transducer elements 104 may be comprised of a piezoelectric material. When a voltage is applied to a piezoelectric crystal, the crystal physically expands and contracts, emitting an ultrasonic wave. In this way, transducer elements 104 may convert electronic transmit signals into acoustic transmit beams.

After the elements 104 of the probe 106 emit pulsed ultrasonic signals into a body (of a patient), the pulsed ultrasonic signals reflect from structures within an interior of the body, like blood cells or muscular tissue, to produce echoes that return to the elements 104. The echoes are converted into electrical signals, or ultrasound data, by the elements 104 and the electrical signals are received by a receiver 108. The electrical signals representing the received echoes are passed through a receive beamformer 110 that outputs ultrasound data.

The echo signals produced by transmit operation reflect from structures located at successive ranges along the transmitted ultrasonic beam. The echo signals are sensed separately by each transducer element and a sample of the echo signal magnitude at a particular point in time represents the amount of reflection occurring at a specific range. Due to the differences in the propagation paths between a reflecting point P and each element, however, these echo signals are not detected simultaneously. Receiver 108 amplifies the separate echo signals, imparts a calculated receive time delay to each, and sums them to provide a single echo signal which approximately indicates the total ultrasonic energy reflected from point P located at range R along the ultrasonic beam oriented at the angle θ.

The time delay of each receive channel continuously changes during reception of the echo to provide dynamic focusing of the received beam at the range R from which the echo signal is assumed to emanate based on an assumed sound speed for the medium.

Under direction of processor 116, the receiver 108 provides time delays during the scan such that steering of receiver 108 tracks the direction θ of the beam steered by the transmitter and samples the echo signals at a succession of ranges R so as to provide the time delays and phase shifts to dynamically focus at points P along the beam. Thus, each emission of an ultrasonic pulse waveform results in acquisition of a series of data points which represent the amount of reflected sound from a corresponding series of points P located along the ultrasonic beam.

According to some embodiments, the probe 106 may contain electronic circuitry to do all or part of the transmit beamforming and/or the receive beamforming. For example, all or part of the transmit beamformer 101, the transmitter 102, the receiver 108, and the receive beamformer 110 may be situated within the probe 106. The terms “scan” or “scanning” may also be used in this disclosure to refer to acquiring data through the process of transmitting and receiving ultrasonic signals. The term “data” may be used in this disclosure to refer to either one or more datasets acquired with an ultrasound imaging system. A user interface 115 may be used to control operation of the ultrasound imaging system 100, including to control the input of patient data (e.g., patient medical history), to change a scanning or display parameter, to initiate a probe repolarization sequence, and the like. The user interface 115 may include one or more of the following: a rotary element, a mouse, a keyboard, a trackball, hard keys linked to specific actions, soft keys that may be configured to control different functions, and a graphical user interface displayed on a display device 118.

The ultrasound imaging system 100 also includes a processor 116 to control the transmit beamformer 101, the transmitter 102, the receiver 108, and the receive beamformer 110. The processor 116 is in electronic communication (e.g., communicatively connected) with the probe 106. For purposes of this disclosure, the term “electronic communication” may be defined to include both wired and wireless communications. The processor 116 may control the probe 106 to acquire data according to instructions stored on a memory of the processor, and/or memory 120.

The processor 116 controls which of the elements 104 are active and the shape of a beam emitted from the probe 106. The processor 116 is also in electronic communication with the display device 118, and the processor 116 may process the data (e.g., ultrasound data) into images for display on the display device 118. The processor 116 may include a central processor (CPU), according to an embodiment. According to other embodiments, the processor 116 may include other electronic components capable of carrying out processing functions, such as a digital signal processor, a field-programmable gate array (FPGA), or a graphic board. According to other embodiments, the processor 116 may include multiple electronic components capable of carrying out processing functions. For example, the processor 116 may include two or more electronic components selected from a list of electronic components including: a central processor, a digital signal processor, a field-programmable gate array, and a graphic board. According to another embodiment, the processor 116 may also include a complex demodulator (not shown) that demodulates the real RF (radio-frequency) data and generates complex data. In another embodiment, the demodulation can be carried out earlier in the processing chain. The processor 116 is adapted to perform one or more processing operations according to a plurality of selectable ultrasound modalities on the data. In one example, the data may be processed in real-time during a scanning session as the echo signals are received by receiver 108 and transmitted to processor 116. For the purposes of this disclosure, the term "real-time" is defined to include a procedure that is performed without any intentional delay. For example, an embodiment may acquire images at a real-time rate of 7-20 frames/sec and/or may acquire volumetric data at a suitable volume rate. The ultrasound imaging system 100 may acquire 2D data of one or more planes at a significantly faster rate. However, it should be understood that the real-time frame-rate may be dependent on the length of time that it takes to acquire each frame of data for display. Accordingly, when acquiring a relatively large amount of data, the real-time frame-rate may be slower. Thus, some embodiments may have real-time frame-rates or volume rates that are considerably faster than 20 frames/sec (or volumes/sec) while other embodiments may have real-time frame-rates or volume rates slower than 7 frames/sec (or volumes/sec). The data may be stored temporarily in a buffer (not shown) during a scanning session and processed in less than real-time in a live or off-line operation. Some embodiments of the invention may include multiple processors (not shown) to handle the processing tasks that are handled by processor 116 according to the exemplary embodiment described hereinabove. For example, a first processor may be utilized to demodulate and decimate the RF signal while a second processor may be used to further process the data, for example by augmenting the data as described further herein, prior to displaying an image. It should be appreciated that other embodiments may use a different arrangement of processors.

The ultrasound imaging system 100 may continuously acquire data at a frame-rate or volume rate of, for example, 10 Hz to 30 Hz (e.g., 10 to 30 frames per second). Images generated from the data (which may be 2D images or 3D renderings) may be refreshed at a similar frame-rate on display device 118. Other embodiments may acquire and display data at different rates. For example, some embodiments may acquire data at a frame-rate or volume rate of less than 10 Hz or greater than 30 Hz depending on the size of the frame and the intended application. A memory 120 is included for storing processed frames or volumes of acquired data. In an exemplary embodiment, the memory 120 is of sufficient capacity to store at least several seconds' worth of frames or volumes of ultrasound data. The frames or volumes of data are stored in a manner to facilitate retrieval thereof according to its order or time of acquisition. The memory 120 may comprise any known data storage medium.

In various embodiments of the present invention, data may be processed in different mode-related modules by the processor 116 (e.g., B-mode, Color Doppler, M-mode, Color M-mode, spectral Doppler, Elastography, TVI, strain, strain rate, and the like) to form 2D or 3D data. For example, one or more modules may generate B-mode, color Doppler, M-mode, color M-mode, spectral Doppler, Elastography, TVI, strain, strain rate, and combinations thereof, and the like. As one example, the one or more modules may process color Doppler data, which may include traditional color flow Doppler, power Doppler, HD flow, and the like. The image lines, frames, and/or volumes are stored in memory and may include timing information indicating a time at which the image lines, frames, and/or volumes were stored in memory. The modules may include, for example, a scan conversion module to perform scan conversion operations to convert the acquired data from beam space coordinates to display space coordinates. A video processor module may be provided that reads the acquired images from a memory and displays an image in real time while a procedure (e.g., ultrasound imaging) is being performed on a patient. The video processor module may include a separate image memory, and the ultrasound images may be written to the image memory in order to be read and displayed by display device 118.

In various embodiments of the present disclosure, one or more components of ultrasound imaging system 100 may be included in a portable, handheld ultrasound imaging device. For example, display device 118 and user interface 115 may be integrated into an exterior surface of the handheld ultrasound imaging device, which may further contain processor 116 and memory 120. Probe 106 may comprise a handheld probe in electronic communication with the handheld ultrasound imaging device to collect raw ultrasound data. Transmit beamformer 101, transmitter 102, receiver 108, and receive beamformer 110 may be included in the same or different portions of the ultrasound imaging system 100. For example, transmit beamformer 101, transmitter 102, receiver 108, and receive beamformer 110 may be included in the handheld ultrasound imaging device, the probe, and combinations thereof.

After performing a two-dimensional or three-dimensional ultrasound scan, a block of data (which may be two-dimensional or three-dimensional) comprising scan lines and their samples is generated. After back-end filters are applied, a process known as scan conversion is performed to transform the data block into a displayable bitmap image with additional scan information such as depths, angles of each scan line, and so on. During scan conversion, an interpolation technique is applied to fill missing holes (i.e., pixels) in the resulting image. These missing pixels occur because each element of the block should typically cover many pixels in the resulting image. For example, in current ultrasound imaging systems, a bicubic interpolation is applied which leverages neighboring elements of the block. As a result, if the block is relatively small in comparison to the size of the bitmap image, the scan-converted image will include areas of less than optimal or low resolution, especially for areas of greater depth.

Figure 2:
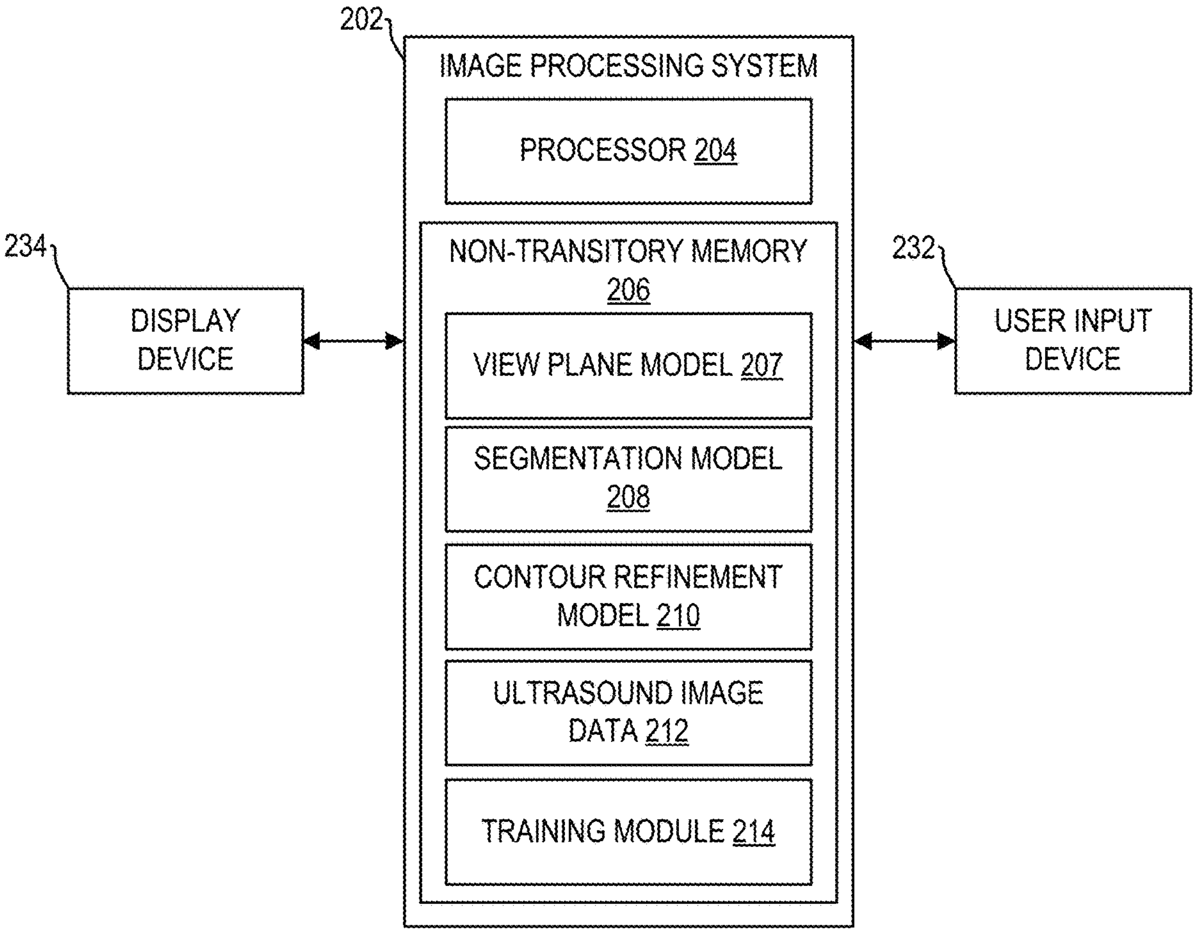
FIG. 2 is a block diagram showing an example image processing system.

Referring to FIG. 2, an image processing system 202 is shown, in accordance with an exemplary embodiment. In some embodiments, image processing system 202 is incorporated into the ultrasound imaging system 100. For example, the image processing system 202 may be provided in the ultrasound imaging system 100 as the processor 116 and memory 120. In some embodiments, at least a portion of image processing system 202 is included in a device (e.g., edge device, server, etc.) communicably coupled to the ultrasound imaging system via wired and/or wireless connections. In some embodiments, at least a portion of image processing system 202 is included in a separate device (e.g., a workstation), which can receive ultrasound data (such as images and/or 3D volumes) from the ultrasound imaging system or from a storage device which stores the images/data generated by the ultrasound imaging system. Image processing system 202 may be operably/communicatively coupled to a user input device 232 and a display device 234. In one example, the user input device 232 may comprise the user interface 115 of the ultrasound imaging system 100, while the display device 234 may comprise the display device 118 of the ultrasound imaging system 100.

Image processing system 202 includes a processor 204 configured to execute machine readable instructions stored in non-transitory memory 206. Processor 204 may be single core or multi-core, and the programs executed thereon may be configured for parallel or distributed processing. In some embodiments, the processor 204 may optionally include individual components that are distributed throughout two or more devices, which may be remotely located and/or configured for coordinated processing. In some embodiments, one or more aspects of the processor 204 may be virtualized and executed by remotely-accessible networked computing devices configured in a cloud computing configuration.

Non-transitory memory 206 may store a view plane model 207, a segmentation model 208, a contour refinement model 210, ultrasound image data 212, and a training module 214.

Each of the view plane model 207, the segmentation model 208, and the contour refinement model 210 may include one or more machine learning models, such as deep learning networks, comprising a plurality of weights and biases, activation functions, loss functions, gradient descent algorithms, and instructions for implementing the one or more deep neural networks to process input ultrasound images. Each of the view plane model 207, the segmentation model 208, and the contour refinement model 210 may include trained and/or untrained neural networks and may further include training routines, or parameters (e.g., weights and biases), associated with one or more neural network models stored therein.

The view plane model 207 may thus include one or more machine learning models configured to process input ultrasound images (which may include 3D renderings) to identify a view plane of interest within a volume of ultrasound data. As will be explained in more detail below, during a pelvic examination, the view plane of interest may be a view plane that includes a minimal hiatal dimension (MHD), referred to as an MHD plane. The view plane model 207 may receive selected frames of a volume of ultrasound data and process the selected frames to identify the MHD plane within the volume of ultrasound data. The view plane model 207 may include a hybrid neural network (e.g., convolutional neural network (CNN)) architecture including 3D convolution layers, a flattening layer, and a 2D neural network (e.g., a CNN such as a UNet). The view plane model 207 may output a 2D segmentation mask that identifies the location of the view plane of interest within the volume of ultrasound data.

The segmentation model 208 may include one or more machine learning models, such as a neural network, configured to process an input ultrasound image to identify an anatomical ROI in the input ultrasound image. For example, as explained in more detail below, the segmentation model 208 may be deployed during a pelvic examination in order to identify the levator hiatus in an input ultrasound image. In some examples, the input ultrasound image may be an image including the view plane identified by the view plane model 207, e.g., the MHD plane. The segmentation model 208 may process the input ultrasound image to output a segmentation (e.g., mask) identifying the anatomical ROI in the input ultrasound image. However, some anatomical features, such as the levator hiatus, may be difficult to accurately identify in a precise manner given patient to patient variability in the size and shape of the anatomical feature. Thus, the initial segmentation output by the segmentation model 208 is used as a guide to map a predefined template to the anatomical ROI in the given ultrasound image to form an adjusted segmentation template that can be entered as input to the contour refinement model 210.

The contour refinement model 210 may include one or more machine learning models, such as a neural network, configured to process the input ultrasound image (e.g., the same image used as input to the segmentation model) and the adjusted segmentation template to identify the anatomical ROI in the input ultrasound image more accurately. The identified anatomical ROI (e.g., the segmentation output by the contour refinement model 210) may be used to generate a border/contour of the anatomical ROI that may then be assessed to measure aspects of the anatomical ROI.

The ultrasound image data 212 may include 2D images and/or 3D volumetric data, from which 3D renderings and 2D images/slices may be generated, captured by the ultrasound imaging system 100 of FIG. 1 or another ultrasound imaging system. The ultrasound image data 212 may include B-mode images, Doppler images, color Doppler images, M-mode images, etc., and/or combinations thereof. Images and/or volumetric ultrasound data saved as part of ultrasound image data 212 may be used to train the view plane model 207, the segmentation model 208, and/or the contour refinement model 210, as explained in more detail below, and/or be entered into the view plane model 207, the segmentation model 208, and/or the contour refinement model 210 to generate the output utilized to perform the automated ultrasound exam, as will be explained in more detail below with respect to FIGS. 7 and 8.

The training module 214 may comprise instructions for training one or more of the deep neural networks stored in the view plane model 207, the segmentation model 208, and/or the contour refinement model 210. In some embodiments, training module 214 includes instructions for implementing one or more gradient descent algorithms, applying one or more loss functions, and/or training routines, for use in adjusting parameters of one or more deep neural networks of the view plane model 207, the segmentation model 208, and/or the contour refinement model 210. In some embodiments, training module 214 includes instructions for intelligently selecting training data pairs from ultrasound image data 212. In some embodiments, training data pairs comprise pairs of input data and ground truth data. The input data may include one or more ultrasound images. For example, to train the view plane model 207, the input data may include, for each pair of input data and ground truth data, a set of 3D ultrasound images (e.g., three or more 3D ultrasound images, such as nine 3D ultrasound images) selected from a volume of ultrasound data. For each set of 3D ultrasound images, the corresponding ground truth data used to train the view plane model 207 may include a segmentation mask (e.g., generated by an expert) indicating the location, within the volume of ultrasound data, of the view plane of interest. The view plane model 207 may be updated based on a loss function between each segmentation mask output by the view plane model and the corresponding ground truth segmentation mask.

To train the segmentation model 208, the input data may include, for each pair of input data and ground truth data, an ultrasound image of the view plane of interest. The corresponding ground truth data may include an expert-labeled segmentation of the anatomical ROI within the ultrasound image of the view plane of interest. The segmentation model 208 may be updated based on a loss function between each segmentation output by the segmentation model and the corresponding ground truth segmentation.

To train the contour refinement model 210, the input data may include, for each pair of input data and ground truth data, an ultrasound image of the view plane of interest and an adjusted segmentation template of an anatomical ROI within the ultrasound image (e.g., a template transformed using the segmentation output for model 208, as explained above), and the corresponding ground truth data may include an expert-labeled segmentation of the anatomical ROI within the ultrasound image of the view plane of interest. In some examples, the segmentation model may be trained and validated, and then the segmentation model may be deployed using the training images for training the contour refinement model to generate a plurality of segmentations that are each used to adjust the template segmentation. These adjusted segmentation templates may be used with the training images as input to train the contour refinement model. The contour refinement model 210 may be updated based on a loss function between each segmentation output by the contour refinement model and the corresponding ground truth segmentation. The output (segmentation) of the segmentation model 208 may be used as a guiding map to position a pre-defined (and fixed) template of the levator hiatus to the ultrasound image under consideration. The matched template is expected to act as an additional guidance input to the contour refinement model 210, which also takes in the original ultrasound image as an input. The corresponding ground truth data may include an expert-labeled segmentation of the anatomical ROI within the ultrasound image of the view plane of interest. The contour refinement model 210 may be updated based on a loss function between each segmentation output by the contour refinement model and the corresponding ground truth segmentation. Morphological operations are performed on the resulting segmentation output to further smoothen and refine the contour.

The segmentation model 208 and the contour refinement model 210 may be separate models/networks that are trained independently of one another. For example, the neural network of the segmentation model 208 may have different weights/biases than the neural network of the contour refinement model 210. Further, while in some examples the contour refinement model 210 may be trained using output of the segmentation model 208, the contour refinement model 210 may be trained independently from the segmentation model 208 because the contour refinement model 210 may use a different loss function than the segmentation model 208 and/or the loss function applied during training of the contour refinement model 210 does not directly take into account the output from the segmentation model 208.

In some embodiments, the non-transitory memory 206 may include components included in two or more devices, which may be remotely located and/or configured for coordinated processing. For example, at least some of the images stored as part of the ultrasound image data 212 may be stored in an image archive, such as a picture archiving and communication system (PACS). In some embodiments, one or more aspects of the non-transitory memory 206 may include remotely-accessible networked storage devices configured in a cloud computing configuration.

In some embodiments, the training module 214 is not disposed at the image processing system 202 and the view plane model 207, the segmentation model 208, and/or the contour refinement model 210 may be trained on an external device. The view plane model 207, the segmentation model 208, and/or the contour refinement model 210 on the image processing system 202 thus include trained and validated network(s).

User input device 232 may comprise one or more of a touchscreen, a keyboard, a mouse, a trackpad, a motion sensing camera, or other device configured to enable a user to interact with and manipulate data within image processing system 202. In one example, user input device 232 may enable a user to make a selection of a view plane thickness and initiate a workflow for automatically identifying a view plane via view plane model 207, segmenting a region of interest via the segmentation model 208 and contour refinement model 210, and performing automated measurements based on the segmentation.

Display device 234 may include one or more display devices utilizing virtually any type of technology. In some embodiments, display device 234 may comprise a computer monitor, and may display ultrasound images. Display device 234 may be combined with processor 204, non-transitory memory 206, and/or user input device 232 in a shared enclosure, or may be peripheral display devices and may comprise a monitor, touchscreen, projector, or other display device known in the art, which may enable a user to view ultrasound images produced by an ultrasound imaging system, and/or interact with various data stored in non-transitory memory 206.

It should be understood that image processing system 202 shown in FIG. 2 is for illustration, not for limitation. Another appropriate image processing system may include more, fewer, or different components.

FIG. 3 schematically illustrates a process 300 for identifying a view plane of interest using a view plane model, such as view plane model 207 of FIG. 2. Process 300 may be carried out according to instructions stored in memory of a computing device, such as memory 206 of image processing system 202, as part of an automated ultrasound exam, such as an automated pelvic exam. As explained above with respect to FIG. 2, the view plane model may take a plurality of 3D images as input in order to generate a segmentation mask that identifies a location of a view plane of interest within a volume of ultrasound data. Thus, process 300 includes selection of a plurality of 3D images 304 from a volume 302 of ultrasound data. The volume 302 may be acquired with an ultrasound probe positioned to image an anatomical neighborhood that includes an anatomical ROI viewable in the view plane of interest. For example, when process 300 is applied during a pelvic exam, the anatomical neighborhood may include the pelvis of a patient and the anatomical ROI may include the levator hiatus viewed in a plane of minimal hiatal dimension (e.g., the MHD plane).

Each image of the plurality of 3D images 304 may correspond to a different slice of ultrasound data (with the slice extending in the elevation plane, which may be referred to as the sagittal plane), and each slice may be positioned at a different position along the azimuth direction, while the view plane of interest may extend in the azimuth direction (e.g., in the axial plane) and thus include ultrasound data from each of the plurality of 3D images. The plurality of 3D images 304 may be selected according to a suitable process. For example, the plurality of 3D images 304 may be selected automatically (e.g., by the computing device). In some examples, the plurality of 3D images 304 may be selected based on user input identifying an initial estimate of the location of the view plane within the volume 302. For example, the operator of the ultrasound probe may enter a user input indicating a location of the view plane of interest within a selected 3D ultrasound image. The computing device may then select the plurality of 3D images 304 based on the user-specified location of the view plane of interest and/or the 3D image selected by the user. For example, the plurality of 3D images 304 may include the 3D image selected by the user and one or more additional 3D images near the 3D image selected by the user (e.g., the slices adjacent to the 3D image selected by the user). While FIG. 3 shows three 3D ultrasound images being selected from the volume 302, it is to be appreciated that more than three 3D images may be selected (e.g., 5 images, 9 images, etc.).

The plurality of 3D images 304 are combined into a stacked set of 3D images 306. The plurality of 3D images may be concatenated or combined as multiple layers to form the stacked set of 3D images 306. The stacked set of 3D images 306 is entered as input to a view plane model 307, which is a non-limiting example of view plane model 207 of FIG. 2. The view plane model 307 includes a set of 3D convolutional layers 308. The stacked set of 3D images 306 is entered as input to the set of 3D convolutional layers 308, where multiple rounds (e.g., two or three) of 3D convolutions may be performed on the stacked set of 3D images 306. The output from the set of 3D convolutional layers 308, which may be a 3D tensor, is passed to a flattening layer 310 that flattens the output to 2D, thereby forming a 2D tensor. The output from the flattening layer 310 (e.g., the 2D tensor) is then entered into a 2D neural network 312, herein a 2D UNet. The 2D neural network 312 outputs a 2D segmentation mask 314. The 2D segmentation mask 314 indicates the location of the view plane of interest relative to one of the 3D images of the plurality of 3D images 304. In the specific example shown in FIG. 3, the 2D segmentation mask 314 shows the location of the MHD plane (e.g., the light gray line extending across the mask) as well as the location of relevant anatomical features (e.g., the levator ani muscle and the inferior pubic rami, shown by the lighter gray and white marks on the mask) within the volume 302. By using the hybrid architecture shown in FIG. 3 (e.g., a relatively small set of 3D convolutional layers and a 2D neural network), 3D input may be used while reducing the processing and/or memory required for a full 3D neural network.

FIG. 4 shows example 3D images 400 including a plurality of unlabeled 3D images 402 and a plurality of labeled 3D images 404 showing locations of a view plane of interest relative to each 3D image, as determined from 2D segmentation masks output from the view plane model described herein. The plurality of unlabeled 3D images 402 may be slices from different volumes of the same anatomical neighborhood (e.g., the pelvis of different patients). Images from each volume are entered as input to the view plane model, as explained above, which outputs a respective 2D segmentation mask that may be applied to generate the labels shown in the plurality of labeled 3D images 404. For example, a first 3D image 406 may be one 3D image of a volume entered as input to the view plane model, which may output a segmentation mask that identifies the view plane of interest. The view plane of interest is shown by a view plane indicator 408 superimposed on a labeled version 407 of the first 3D image 406. In addition to depicting the location of the view plane of interest, the view plane indicator 408 may indicate the thickness of the slice that will be used to generate a 3D image of the view plane of interest may be illustrated (e.g., the distance between the two lines of the view plane indicator 408 may indicate the thickness), as explained in more detail below.

In this way, the view plane model may identify a view plane of interest (e.g., the MHD plane) within a volume of ultrasound data. Once the view plane of interest is identified, a 3D image of that view plane may be rendered and used for further processing in the automated ultrasound exam. In contrast, prior manual ultrasound exams may demand the operator identify the location of the view plane of interest on a selected 3D image (e.g., first 3D image 406) by applying a rendering box to the image, such as by drawing a box that encompasses the location of the view plane. As appreciated from the view plane indicator 408 and the other view plane lines shown in FIG. 4, the view plane of interest may not extend in a straight line and thus the process of identifying the view plane using a rectangular box may be prone to errors and/or require excess user time and effort in correctly placing the rendering box. In contrast, the view plane model may identify the view plane as a line extending at any angle as dictated by the location of the view plane within the volume, which may be more accurate and less demanding on the user.

FIG. 5 shows a process 500 for segmenting an anatomical ROI within a an image of a view plane of interest using a segmentation model and a contour refinement model, such as segmentation model 208 and contour refinement model 210 of FIG. 2. Process 500 may be carried out according to instructions stored in memory of a computing device, such as memory 206 of image processing system 202, as part of an automated ultrasound exam, such as an automated pelvic exam. As explained above, an image of a view plane of interest may be extracted from a volume of ultrasound data, such as image 502, which in the example shown is an image of the MHD plane. The image 502 may be a 2D image, as shown. However, in some examples, the image 502 may be 3D rendering. The image 502 is entered as input to a segmentation model at 504 (e.g., segmentation model 208). The example of process 500 shown in FIG. 5 is performed as part of a pelvic exam, and thus the segmentation model may be trained to segment the levator hiatus in the image 502. The segmentation model may output an initial segmentation 506 of the anatomical ROI (herein the levator hiatus). However, some anatomical regions, such as the levator hiatus, may exhibit patient to patient variability in appearance. Further, surrounding anatomical features may make the overall shape of the anatomical ROI difficult to correctly identify using a typical segmentation model. Thus, the initial segmentation 506 may be used to correct a template segmentation 508. The template segmentation 508 may be generated from a plurality of prior segmentations of the anatomical ROI and may represent an average or ideal shape and size of the anatomical ROI. The initial segmentation 506 is used to map the pre-determined (as explained above) template segmentation 508 using a transformation matrix, for example. The mapping may result in a corrected segmentation template that has been adjusted (based on the initial segmentation) in length, width, and/or shape (e.g., areas of the anatomical ROI obscured by other tissue may be filled in) but not in other aspects (e.g., skew, rotation, etc., may be maintained).

The corrected segmentation template may be entered as input along with the image 502 to a contour refinement model at 510 (e.g., the contour refinement model 210 of FIG. 2), where the contour refinement model is trained to output a refined segmentation 512 of the anatomical ROI, which may be used to generate a contour (e.g., border) of the anatomical ROI that may be overlaid on the image. For example, a labeled version 514 of the image 502 is shown, including a contour 516 of the anatomical ROI depicted as an overlay on the labeled version 514 of the image. The contour may be used to measure one or more aspects of the anatomical ROI, such as diameter, circumference, area, etc.

FIG. 6 shows a plurality of example images 600 of an anatomical ROI, herein the levator hiatus as shown in the MHD plane. The plurality of example images 600 includes a first image 602, which may be a 2D image or a 3D rendering of the MHD plane of a volume of ultrasound data of a first patient. The first image 602 may be entered as input to the segmentation model and the contour refinement model as explained above with respect to FIG. 5. The output of the contour refinement model may be used to generate a contour 606 that is overlaid on a labeled version 604 of the first image 602. In addition to the contour 606, lines may be placed at the largest diameter in both the anterior-posterior and lateral directions. The plurality of example images 600 includes a second image 608, which may be a 2D image or a 3D rendering of the MHD plane of a volume of ultrasound data of a second patient. The second image 608 may be entered as input to the segmentation model and the contour refinement model as explained above with respect to FIG. 5. The output of the contour refinement model may be used to generate a contour 612 that is overlaid on a labeled version 610 of the second image 608. As appreciated by comparing contour 606 to contour 612, different patients may exhibit variances in the shape and size of the anatomical ROI, and thus the mapping of the initial segmentation output by the segmentation model and re-identification of the boundary of the anatomical ROI using the corrected segmentation template via the contour refinement model may enable more accurate determination of the boundaries of the anatomical ROI, and thus more accurate measurements of the anatomical ROI.

FIG. 7 is a flow chart illustrating an example method 700 for identifying a view plane of interest in one or more volumes of ultrasound data according to an embodiment of the present disclosure. Method 700 is described with regard to the systems and components of FIGS. 1-2, though it should be appreciated that the method 700 may be implemented with other systems and components without departing from the scope of the present disclosure. Method 700 may be carried out according to instructions stored in non-transitory memory of a computing device, such as image processing system 202 of FIG. 2. In a non-limiting example, process 300 of FIG. 3 may be carried out according to method 700.

At 702, method 700 includes acquiring ultrasound data of a patient. The ultrasound data may be acquired with an ultrasound probe (e.g., ultrasound probe 106 of FIG. 1). The ultrasound data may be processed to generate one or more displayable images that may be displayed on a display device (e.g., display device 118). The ultrasound data may be processed to generate 2D images and/or 3D renderings that may be displayed in real-time as images are acquired and/or may be displayed in a more persistent manner in response to user input (e.g., an indication to freeze on a given image). At 704, user input is received specifying a view plane of interest and a desired slice thickness of the view plane of interest on a selected displayed ultrasound image frame. For example, as explained above, an operator of the ultrasound probe may be executing a patient exam according to an exam workflow that dictates certain measurements of an anatomical ROI be taken, such as measurements of the levator hiatus during a pelvic exam. The anatomical ROI may extend in a view plane not easily generated by standard 2D ultrasound imaging and thus the exam workflow may include an automatic identification of the view plane within a volumetric (e.g., 3D) ultrasound dataset. The operator may trigger the automatic identification of the view plane by providing an indication of a length and slice thickness of the view plane on a selected ultrasound image. For example, the user may draw a line along the currently displayed ultrasound image indicating a length of the view plane of interest. The user may also specify the desired final slice thickness of the rendering of the view plane of interest via the user input. The user-drawn line and identified slice thickness may be used to trigger a 4D acquisition and identify the view plane of interest on the first frame of the 4D acquisition (e.g., volumetric acquisition over time).

At 706, method 700 includes acquiring volumetric ultrasound data with the patient in a first condition. Some exam workflows, such as pelvic exams, may dictate that an anatomical neighborhood of the patient (e.g., the pelvis) be imaged while the patient performs muscle contractions, releases, breath holds, or other maneuvers. Thus, the operator may control the ultrasound probe to acquire a volumetric ultrasound dataset of the anatomical neighborhood while the patient is instructed to assume/hold the first condition, which may be a breath hold such as Valsalva, for example.

At 708, once the volumetric ultrasound dataset has been acquired, selected frames of the volumetric ultrasound data are entered as input into a view plane model, such as view plane model 207 of FIG. 2. The selected frames may include a suitable number of frames (e.g., 3, 6, 9, or another suitable number) that is more than one frame. As explained previously with respect to FIG. 3, the selected ultrasound frames (which are 3D images) are stacked and entered as a joint input to an input layer of a set of 3D convolutional layers, which may perform a series of 3D convolutions on the input images and output the 3D tensor from the convolutional layers to a flattening layer that may flatten the 3D tensor to a 2D tensor. The 2D tensor is then passed through a 2D neural network, which outputs the 2D segmentation mask. At 710, a 2D segmentation mask is received as output from the view plane model. The 2D segmentation mask may indicate the location of the view plane of interest relative to one of the selected ultrasound frames. When the patient exam is a pelvic exam as explained herein, the 2D segmentation mask may indicate the location of the MHD plane as well as the location of the anatomical features defining the MHD plane (e.g., the levator ani), as indicated at 712.

At 714, the location of the view plane (as identified by the 2D segmentation mask) may be displayed as a view plane indicator that is overlaid on one of the selected ultrasound image frames. In this way, the operator may view the identified location of the view plane of interest. If the operator does not agree with the identified location of the view plane of interest, the operator may enter user input (e.g., moving the view plane indicator as desired) and method 700 may include adjusting the view plane based on the entered user input at 716.

At 718, method 700 determines if the exam workflow includes additional patient conditions. For example, after the first patient condition, the exam workflow may dictate that a new volume of ultrasound data be acquired with the patient in a second condition that is different than the first condition (e.g., muscle contraction). If the workflow includes additional patient conditions that have not been imaged, method 700 proceeds to 720 to acquire volumetric ultrasound data with the patient in the next condition. The acquisition of the volumetric data with the patient in the next condition may include, before the volumetric data is acquired, reception of user input specifying the view plane length and desired slice thickness on a selected image. The user input may trigger the next volumetric acquisition. Method 700 then loops back to 708 and repeats the identification of the view plane of interest in the newly-acquired volumetric ultrasound dataset. If it is instead determined at 718 that the workflow does not include additional patient conditions (e.g., all patient conditions have been imaged) and/or that the exam is complete, method 700 ends.

FIG. 8 is a flow chart illustrating an example method 800 for identifying an anatomical ROI in a view plane image according to an embodiment of the present disclosure. Method 800 is described with regard to the systems and components of FIGS. 1-2, though it should be appreciated that the method 800 may be implemented with other systems and components without departing from the scope of the present disclosure. Method 800 may be carried out according to instructions stored in non-transitory memory of a computing device, such as image processing system 202 of FIG. 2. In a non-limiting example, process 500 of FIG. 5 may be carried out according to method 800.

At 802, method 800 includes obtaining a view plane image. The view plane image may be obtained by extracting the view plane image from a volumetric ultrasound dataset based on a mask output by a view plane model (such as view plane model 207). The view plane image may be extracted based on one of the 2D segmentation masks output as part of method 700 described above. For example, the volumetric ultrasound dataset may be the volumetric ultrasound dataset acquired as part of method 700 with the patient in the first condition. The 2D segmentation mask may indicate the location of the view plane of interest within the volumetric ultrasound data, which may be the MHD plane as explained above. The view plane image may be extracted by extracting the ultrasound data from the volumetric ultrasound dataset that lies in the plane identified by the 2D segmentation mask, as well as ultrasound data adjacent to the plane (e.g., above and below) as dictated by the user-specified slice thickness (as explained above with respect to FIG. 7). The view plane image may be a 3D rendering of the view plane of interest, at least in some examples. In other examples, the view plane image may be a 2D image.

At 804, the view plane image is entered as input to a segmentation model, such as segmentation model 208. The segmentation model may be a deep learning model (e.g., neural network) trained to output a segmentation of an anatomical ROI within the view plane image, such as the levator hiatus. In some examples, the deep learning model may be trained to segment additional structures to improve accuracy and/or model training, but the anatomical ROI may be the only segmented structure that is output to the user. Thus, at 806, method 800 includes receiving a segmentation of the anatomical ROI from the segmentation model. As explained previously, the anatomical ROI may exhibit patient to patient variation that may make an accurate segmentation of the anatomical ROI for each patient difficult for a deep learning model to perform. Accordingly, the segmentation output by the segmentation model (which may be an initial segmentation of the anatomical ROI) may be used to adjust a template of the anatomical ROI, as indicated at 808. The template of the anatomical ROI may be an average/mean shape and/or size of the anatomical ROI determined based on a plurality of patients. For example, the training data used to train the segmentation model may include ground truth data comprising expert-labeled images of a plurality of patients, where the labels indicate the boundaries of the anatomical ROI in each image. The labels/boundaries generated by the experts may be averaged using a suitable process, such as a Procrustes analysis, to identify the mean shape of the anatomical ROI. The initial segmentation may be used to adjust the pre-determined template with a transformation matrix. The template may be adjusted as dictated by the initial segmentation in the x- and y-directions (e.g., stretched and/or squeezed) but may not be rotated or have other more complex transformations applied. Once the template is adjusted based on the segmentation, an adjusted segmentation template is formed.

At 810, the view plane image and the adjusted segmentation template are entered as input to a contour refinement model (e.g., contour refinement model 210 of FIG. 2). The view plane image entered as input to the contour refinement model is the same view plane image originally entered as input into the segmentation model. The contour refinement model may be trained to output a segmentation of the anatomical ROI within the view plane image using not only the view plane image but also the adjusted segmentation template, which may result in a more accurate segmentation than the initial segmentation output by the segmentation model. At 812, a refined segmentation of the anatomical ROI is received as output from the contour refinement model. In some examples, one or more minor morphological operations may be performed on the refined segmentation to further smoothen the contour of the refined segmentation.

At 814, a contour generated from the refined segmentation is displayed as an overlay on the view plane image. The contour may be the border/boundary of the refined segmentation. By displaying the contour as overlay on the view plane image (where the contour is aligned with the anatomical ROI within the view plane image so that the contour marks the border of the anatomical ROI), the operator of the ultrasound system or other clinician viewing the view plane image may determine if the contour is accurate and sufficiently defines the anatomical ROI within the view plane image.

At 816, one or more measurements may be performed based on the contour. For example, the area, circumference, diameter(s) of the anatomical ROI may be measured automatically based on the contour. To determine the diameter(s), one or more measurement lines may be placed across the contour, e.g., a first measurement line may be placed at the longest segment of the contour and a second measurement line may be placed at the widest segment of the contour. The measurements may be displayed for user review and/or saved as part of the patient exam.

At 818, method 800 determines if additional volumes are available for analysis. As explained previously, during pelvic exams, multiple volumes of ultrasound data may be acquired at different patient conditions. If an additional volume of ultrasound data is available for analysis (e.g., a second volumetric ultrasound dataset acquired during a second condition, as explained above with respect to FIG. 7), method 800 proceeds to 820 to advance to the next volume, and then method 800 loops back to 802 to extract a view plane image from the next volume, identify the anatomical ROI within the view plane image of the next volume, and perform one or more measurements of the anatomical ROI within the view plane image of the next volume. In this way, the dimensions or other measurements of the anatomical ROI may be assessed across multiple patient conditions. If instead at 818 it is determined that no more volumes are available to assess (e.g., each acquired volume has been assessed), method 800 ends.

FIGS. 9 and 10 show example graphical user interfaces (GUIs) that may be displayed during an automated ultrasound exam carried out according to methods 700 and 800. FIG. 9 shows a first example GUI 900 that may displayed during a first portion of an automated pelvic exam of a patient. The first example GUI 900 includes a first 3D ultrasound image 902. The first 3D ultrasound image may be a midsagittal slice of a first volumetric ultrasound dataset acquired with the patient in a first condition. A first view plane indicator 904 is displayed as an overlay on the first 3D ultrasound image 902. The first view plane indicator 904 may depict the location of the view plane of interest relative to the first 3D ultrasound image 902, where the location of the view plane of interest is identified based on output from the view plane model. A first slice thickness line 906 is also displayed. The first slice thickness line 906 may indicate the slice thickness of a first view plane image that is rendered from the first volumetric dataset based on the location of the view plane of interest. In the illustrated example, the view plane of interest is the MHD plane.

The first example GUI 900 further includes the first view plane image 910, which is a 3D rendering of an axial slice of data from the first volumetric ultrasound dataset, where the slice extends in the view plane as defined by the first view plane indicator 904 and has a thickness defined by the first slice thickness line 906. The first view plane image 910 includes, as an overlay, a first contour 912 showing the border of the anatomical ROI (herein the levator hiatus) as determined from the output of the segmentation model and the contour refinement model, as well as two measurement lines. The border and measurement lines of the anatomical ROI may be used to generate measurements of the anatomical ROI, which are shown in a first measurement box 914. As shown, the anatomical ROI in the first volumetric ultrasound dataset has a first area (e.g., 26.5 $cm^2$), a first anterior-posterior (AP) diameter (e.g., 72.3 mm), and a first lateral (lat) diameter (e.g., 48.1 mm).

FIG. 10 shows a second example GUI 920 that may displayed during a second portion of the automated pelvic exam. The second example GUI 920 includes a second 3D ultrasound image 922. The second 3D ultrasound image may be a midsagittal slice of a second volumetric ultrasound dataset acquired with the patient in a second condition. A second view plane indicator 924 is displayed as an overlay on the second 3D ultrasound image 922. The second view plane indicator 924 may depict the location of the view plane of interest relative to the second 3D ultrasound image 922, where the location of the view plane of interest is identified based on output from the view plane model. A second slice thickness line 926 is also displayed. The second slice thickness line 926 may indicate the slice thickness of a second view plane image that is rendered from the second volumetric dataset based on the location of the view plane of interest. In the illustrated example, the view plane of interest is the MHD plane. Because the second example GUI 920 depicts images of the second volumetric ultrasound dataset, which is different than the first volumetric ultrasound dataset, the second view plane indicator 924 may extend at a different angle, from a different starting point, etc., than the first view plane indicator 904, given that the view plane of interest is located in different locations in the first versus the second volumetric ultrasound dataset. In this way, the same anatomical ROI may be shown during different conditions.

The second example GUI 920 further includes the second view plane image 930, which is a 3D rendering of an axial slice of data from the second volumetric ultrasound dataset, where the slice extends in the view plane as defined by the second view plane indicator 924 and has a thickness defined by the second slice thickness line 926. The second view plane image 930 includes, as an overlay, a second contour 932 showing the border of the anatomical ROI (herein the levator hiatus) as determined from the output of the segmentation model and the contour refinement model, as well as two measurement lines. The border and measurement lines of the anatomical ROI may be used to generate measurements of the anatomical ROI, which are shown in a second measurement box 934. As shown, the anatomical ROI in the second volumetric ultrasound dataset has a second area (e.g., 23.8 $cm^2$), a second AP diameter (e.g., 63.7 mm), and a second lat diameter (e.g., 49.6 mm).

A technical effect of executing an automated ultrasound exam including automatically identifying a view plane of interest within a volume of ultrasound data using a view plane model is that the view plane of interest may be identified more accurately and quickly than manual identification of the view plane of interest. Another technical effect of executing the automated ultrasound exam including segmenting an anatomical ROI using two independent segmentation models and an adjusted segmentation template is that the anatomical ROI may be identified quickly and in a more accurate manner than relying on a standard, single segmentation model.

The disclosure also provides support for a method, comprising: identifying a view plane of interest based on one or more 3D ultrasound images, obtaining a view plane image including the view plane of interest from a 3D volume of ultrasound data of a patient, where the one or more 3D ultrasound images are generated from the 3D volume of ultrasound data, segmenting an anatomical region of interest (ROI) within the view plane image to generate a contour of the anatomical ROI, and displaying the contour on the view plane image. In a first example of the method, the view plane of interest includes a minimal hiatal dimension (MHD) plane and the anatomical ROI comprises a levator hiatus. In a second example of the method, optionally including the first example, the method further comprises: identifying a first diameter of the contour and a second diameter of the contour, and displaying the first diameter and the second diameter. In a third example of the method, optionally including one or both of the first and second examples, segmenting the anatomical ROI to generate the contour comprises entering the view plane image as input into a segmentation model trained to output an initial segmentation of the anatomical ROI. In a fourth example of the method, optionally including one or more or each of the first through third examples, segmenting the anatomical ROI to generate the contour further comprises adjusting a template segmentation of the anatomical ROI based on the initial segmentation to generate an adjusted segmentation template and entering the adjusted segmentation template and the view plane image as input to a contour refinement model trained to output a refined segmentation of the anatomical ROI, the contour based on the refined segmentation. In a fifth example of the method, optionally including one or more or each of the first through fourth examples, the segmentation model and the contour refinement model are separate models and are trained independently of one another. In a sixth example of the method, optionally including one or more or each of the first through fifth examples, the template segmentation represents an average segmentation of the anatomical ROI from a plurality of patients. In a seventh example of the method, optionally including one or more or each of the first through sixth examples, identifying the view plane of interest based on the one or more 3D ultrasound images comprises entering the one or more 3D ultrasound images as input to a view plane model trained to output a 2D segmentation mask indicating a location of the view plane of interest within the 3D volume of ultrasound data.

The disclosure also provides support for a system, comprising: a display device, and a computing device operably coupled to the display device and including memory storing instructions executable by a processor to: identify a view plane of interest based on one or more 3D ultrasound images, obtain a view plane image including the view plane of interest from a 3D volume of ultrasound data of a patient, where the one or more 3D ultrasound images are generated from the 3D volume of ultrasound data, segment an anatomical region of interest (ROI) within the view plane image to generate a contour of the anatomical ROI, and display the contour on the view plane image on the display device. In a first example of the system, the memory stores a view plane model trained to identify the view plane of interest using the one or more 3D ultrasound images as input. In a second example of the system, optionally including the first example, the view plane model comprises one or more 3D convolution layers, a flattening layer, and a 2D network. In a third example of the system, optionally including one or both of the first and second examples, the memory stores a segmentation model and a contour refinement model that are deployed to segment the anatomical ROI. In a fourth example of the system, optionally including one or more or each of the first through third examples, the segmentation model is trained to output an initial segmentation of the anatomical ROI using the view plane image as input, and the contour refinement model is trained to output a refined segmentation of the anatomical ROI using the view plane image and an adjusted segmentation template, the adjusted segmentation template including a template segmentation adjusted based on the initial segmentation, and wherein the contour of the anatomical ROI is generated from the refined segmentation. In a fifth example of the system, optionally including one or more or each of the first through fourth examples, the view plane of interest includes a minimal hiatal dimension (MHD) plane and the anatomical ROI comprises a levator hiatus.

The disclosure also provides support for a method for an automated pelvic ultrasound exam, comprising: identifying a minimal hiatal dimension (MHD) plane based on one or more 3D ultrasound images generated from a 3D volume of ultrasound data of a patient, displaying, on a display device, an indicator of a location of the MHD plane relative to one of the one or more 3D ultrasound images, obtaining an MHD image including the MHD plane from the 3D volume of ultrasound data, segmenting a levator hiatus within the MHD image to generate a contour of the levator hiatus, performing one or more measurements of the levator hiatus based on the contour, and displaying, on the display device, results of the one or more measurements and/or displaying the contour on the MHD image. In a first example of the method, the 3D volume of ultrasound data is a first 3D volume of ultrasound data acquired while the patient is in a first condition, and further comprising: identifying the MHD plane based on one or more second 3D ultrasound images generated from a second 3D volume of ultrasound data of the patient acquired while the patient is in a second condition, displaying, on the display device, a second indicator of a second location of the MHD plane relative to one of the one or more second 3D ultrasound images, obtaining a second MHD image including the MHD plane from the second 3D volume of ultrasound data, segmenting the levator hiatus within the second MHD image to generate a second contour of the levator hiatus, performing one or more second measurements of the levator hiatus based on the second contour, and displaying, on the display device, results of the one or more second measurements and/or the second contour on the second MHD image. In a second example of the method, optionally including the first example, identifying the MHD plane based on the one or more 3D ultrasound images comprises entering the one or more 3D ultrasound images as input to a view plane model trained to output a 2D segmentation mask indicating a location of the MHD plane within the 3D volume of ultrasound data. In a third example of the method, optionally including one or both of the first and second examples, segmenting the levator hiatus to generate the contour comprises entering the MHD image as input into a segmentation model trained to output an initial segmentation of the levator hiatus. In a fourth example of the method, optionally including one or more or each of the first through third examples, segmenting the levator hiatus to generate the contour further comprises adjusting a template segmentation of the levator hiatus based on the initial segmentation to generate an adjusted segmentation template and entering the adjusted segmentation template and the MHD image as input to a contour refinement model trained to output a refined segmentation of the levator hiatus, the contour based on the refined segmentation. In a fifth example of the method, optionally including one or more or each of the first through fourth examples, the template segmentation represents an average segmentation of the levator hiatus from a plurality of patients.

When introducing elements of various embodiments of the present disclosure, the articles “a,” “an,” and “the” are intended to mean that there are one or more of the elements. The terms “first,” “second,” and the like, do not denote any order, quantity, or importance, but rather are used to distinguish one element from another. The terms “comprising,” “including,” and “having” are intended to be inclusive and mean that there may be additional elements other than the listed elements. As the terms “connected to,” “coupled to,” etc. are used herein, one object (e.g., a material, element, structure, member, etc.) can be connected to or coupled to another object regardless of whether the one object is directly connected or coupled to the other object or whether there are one or more intervening objects between the one object and the other object. In addition, it should be understood that references to “one embodiment” or “an embodiment” of the present disclosure are not intended to be interpreted as excluding the existence of additional embodiments that also incorporate the recited features.

In addition to any previously indicated modification, numerous other variations and alternative arrangements may be devised by those skilled in the art without departing from the spirit and scope of this description, and appended claims are intended to cover such modifications and arrangements. Thus, while the information has been described above with particularity and detail in connection with what is presently deemed to be the most practical and preferred aspects, it will be apparent to those of ordinary skill in the art that numerous modifications, including, but not limited to, form, function, manner of operation and use may be made without departing from the principles and concepts set forth herein. Also, as used herein, the examples and embodiments, in all respects, are meant to be illustrative only and should not be construed to be limiting in any manner.

The invention claimed is:

1. A method, comprising:

identifying a view plane of interest based on one or more 3D ultrasound images, including entering the one or more 3D ultrasound images as input to a view plane model trained to output a 2D segmentation mask indicating a location of the view plane of interest within a 3D volume of ultrasound data of a patient, wherein the view plane of interest includes a minimal hiatal dimension (MHD) plane and the anatomical ROI comprises a levator hiatus, and wherein entering the one or more 3D ultrasound images as input to the view plane model trained to output the 2D segmentation mask comprises entering a stack of at least two 3D images as input to a set of 3D convolutional layers of the view plane model, the set of 3D convolutional layers configured to generate a 3D tensor from the set of at least two 3D images, the view plane model configured to flatten the 3D tensor to a 2D tensor and generate the segmentation mask from the 2D tensor;

obtaining a view plane image including the view plane of interest from the 3D volume of ultrasound data based on the 2D segmentation mask, wherein the one or more 3D ultrasound images are generated from the 3D volume of ultrasound data;

segmenting an anatomical region of interest (ROI) within the view plane image to generate a contour of the anatomical ROI; and displaying the contour on the view plane image.

2. The method of claim 1, further comprising identifying a first diameter of the contour and a second diameter of the contour, and displaying the first diameter and the second diameter, wherein the view plane of interest model is trained with training data pairs that each include a set of 3D ultrasound images selected from a training 3D volume of ultrasound data and a ground truth segmentation mask indicating a location of the view plane of interest within the training 3D volume.

3. The method of claim 1, wherein segmenting the anatomical ROI to generate the contour comprises entering the view plane image as input into a segmentation model trained to output an initial segmentation of the anatomical ROI.

4. The method of claim 3, wherein segmenting the anatomical ROI to generate the contour further comprises adjusting a template segmentation of the anatomical ROI based on the initial segmentation to generate an adjusted segmentation template and entering the adjusted segmentation template and the view plane image as input to a contour refinement model trained to output a refined segmentation of the anatomical ROI, the contour based on the refined segmentation.

5. The method of claim 4, wherein the segmentation model and the contour refinement model are separate models and are trained independently of one another.

6. The method of claim 4, wherein the template segmentation represents an average segmentation of the anatomical ROI from a plurality of patients.

7. The method of claim 1, wherein a plurality of 3D images are generated from the 3D volume of ultrasound data, and wherein only a portion of the plurality of 3D images is entered as input to the view plane model.

8. A system, comprising:

a display device; and a computing device operably coupled to the display device and including memory storing a view plane model, a segmentation model, a contour refinement model, and instructions executable by a processor to:

identify a view plane of interest based on one or more 3D ultrasound images, the view plane model trained to identify the view plane of interest using the one or more 3D ultrasound images as input, the view plane model comprising one or more 3D convolution layers, a flattening layer, and a 2D network;

obtain a view plane image including the view plane of interest from a 3D volume of ultrasound data of a patient, wherein the one or more 3D ultrasound images are generated from the 3D volume of ultrasound data;

segment an anatomical region of interest (ROI) within the view plane image to generate a contour of the anatomical ROI using the segmentation model and the contour refinement model, wherein the segmentation model is trained to output an initial segmentation of the anatomical ROI using the view plane image as input, and the contour refinement model is trained to output a refined segmentation of the anatomical ROI using the view plane image and an adjusted segmentation template, the adjusted segmentation template including a template segmentation adjusted based on the initial segmentation, and wherein the contour of the anatomical ROI is generated from the refined segmentation; and display the contour on the view plane image on the display device.

9. The system of claim 8, wherein the segmentation model and the contour refinement model are separate models and are trained independently of one another.

10. The system of claim 9, wherein the segmentation model is trained with first training data pairs that each include a training image of the view plane of interest and a ground truth segmentation of the anatomical ROI within the corresponding training image, and wherein the contour refinement model is trained with second training data pairs that each include a training image of the view plane of interest and a ground truth adjusted segmentation template.

11. The system of claim 8, wherein the view plane of interest includes a minimal hiatal dimension (MHD) plane and the anatomical ROI comprises a levator hiatus.

* * * * *